United States Patent
Motwani et al.

(10) Patent No.: US 10,123,970 B2
(45) Date of Patent: *Nov. 13, 2018

(54) TOPICAL RETINOID SOLUTIONS

(75) Inventors: Sanjay Kumar Motwani, Bhopal (IN); Shashikanth P. Isloor, Shimoga (IN); Vinod Arora, Gurgaon (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 93 days.

This patent is subject to a terminal disclaimer.

(21) Appl. No.: 13/320,169

(22) PCT Filed: May 20, 2010

(86) PCT No.: PCT/IB2010/052255
§ 371 (c)(1),
(2), (4) Date: Jun. 25, 2012

(87) PCT Pub. No.: WO2010/134048
PCT Pub. Date: Nov. 25, 2010

(65) Prior Publication Data
US 2012/0259014 A1    Oct. 11, 2012

(30) Foreign Application Priority Data

May 20, 2009  (IN) ............... 1039/DEL/2009
Dec. 31, 2009  (IN) ............... 2759/DEL/2009

(51) Int. Cl.
*A61K 9/00*      (2006.01)
*A61K 31/07*     (2006.01)
*A61K 45/06*     (2006.01)
*A61K 31/203*    (2006.01)

(52) U.S. Cl.
CPC ............ *A61K 9/0014* (2013.01); *A61K 31/07* (2013.01); *A61K 31/203* (2013.01); *A61K 45/06* (2013.01)

(58) Field of Classification Search
CPC ..... A61K 31/07; A61K 31/203; A61K 9/0014
See application file for complete search history.

(56) References Cited

U.S. PATENT DOCUMENTS

| | | | |
|---|---|---|---|
| 3,946,013 A | 3/1976 | Tauscher et al. | |
| 4,322,438 A | 3/1982 | Peck | 424/318 |
| 4,593,046 A | 6/1986 | Gruber | 514/717 |
| 4,727,088 A * | 2/1988 | Scott | A61K 8/0229 424/DIG. 5 |
| 4,888,342 A | 12/1989 | Kligman | 514/419 |
| 5,252,604 A * | 10/1993 | Nagy et al. | 514/559 |
| 5,643,584 A | 7/1997 | Farng et al. | 424/401 |
| 6,277,881 B1 | 8/2001 | Santhanam et al. | 514/529 |
| 6,339,107 B1 | 1/2002 | Belloni | 514/725 |
| 7,211,267 B2 * | 5/2007 | Ashley | 424/401 |
| 7,435,427 B2 | 10/2008 | Vanderbist et al. | 424/439 |
| 2002/0182199 A1 * | 12/2002 | Hoppe et al. | 424/94.1 |
| 2004/0052824 A1 | 3/2004 | Abou Chacra-Vernet et al. | |
| 2005/0129773 A1 * | 6/2005 | Bhatia | A61K 9/14 424/489 |
| 2006/0177392 A1 * | 8/2006 | Walden | A61K 8/36 424/59 |
| 2006/0241078 A1 * | 10/2006 | Ahmed et al. | 514/49 |
| 2007/0104780 A1 | 5/2007 | Lipari et al. | 424/456 |
| 2009/0010968 A1 | 1/2009 | Allart et al. | 424/401 |
| 2012/0259013 A1 | 10/2012 | Motwani et al. | |

FOREIGN PATENT DOCUMENTS

| | | | |
|---|---|---|---|
| CA | 2730787 | 1/2010 | ............... A61K 9/08 |
| EP | 0 184 942 | 8/1990 | ............. A61K 31/20 |
| EP | 0 578 077 | 9/1999 | ............. A61K 31/07 |
| RU | 2168996 | 6/2001 | ............. A61K 31/07 |
| WO | WO 90/14833 | 12/1990 | ............. A61K 31/78 |
| WO | WO 00/25772 | 5/2000 | ........... A61K 31/203 |
| WO | 00/51571 A2 | 9/2000 | |
| WO | WO 2004/087118 | 10/2004 | ............. A61K 31/05 |
| WO | WO 2005/011741 | 2/2005 | ............. A61K 47/48 |

OTHER PUBLICATIONS

Geronikaki et al. Antioxidants and inflammatory disease: synthetic and natural antioxidants with anti-inflammatory activity. Combinatorial Chemistry & High Throughput Screening, 2006, 9, 425-442.*
Drugs.com (Revised 2017).*
Nankervis et al., "Effect of lipid vehicle on the intestinal lymphatic transport of isotretinoin in the rat", *International Journal of Pharmaceutics*, 119(2):173-181 (1995).
Strickley, "Solubilizing Excipients in Oral and Injectable Formulations", *Pharmaceutical Research*, 21(2):201-230 (2004).
Lehman et al., "Percutaneous Absorption of Retinoids: Influence of Vehicle, Light Exposure, and Dose," *Journal of Investigative Dermatology*, 91(1):56-61 (1988).
Final Office Action for U.S. Appl. No. 15/444,491, issued by USPTO dated Apr. 2, 2018.
Chempro (Top-Notch Technology in Production of Oils and Fats) Available from: http://www.chempro.in/fattyacid.htm [accessed on Jan. 21, 2015].
The Peanut Institute (Peanut Oil) Available from: http://www.peanut-institute.org/peanut-products/peanut-oil.asp [accessed on Jan. 21, 2015].
Hammond et al., 2005. Chapter 13: Soybean Oil. In: Shahidi, ed. Bailey's Industrial Oil and Fat Products, 6th Edition. John Wiley & Sons, Inc., 577-653.
Tseng et al., "Inhibition of Conjuctival Transdifferentiation by Topical Retinoids," Investigative Ophthalmology & Visual Science, 28(3):538-542 (1987).
Cremer, Miglyol 812 Available from: http://www.petercremerna.com/products/159339301 [accessed on Sep. 29, 2016].
K S Alexander, "Corn Oil: Pharmaceutical Excipients", *Handbook of Pharmaceutical Excipients*(2017) [Accessed on Mar. 13, 2018] (Available from: https://www.medicinecomplete.com/mc/excipients/current/1001936897.htm?q=corn).
Anonymous, "Aluminium Acetate", *Martindale: The Complete Drug Reference*(2014) [Accessed on Mar. 13, 2018] (Available from: https://www.medicinescomplete.com/mc/martindale/current/296-d.htm?q=astringents&t=search&ss=text&tot=6&p=1#_hit).

(Continued)

*Primary Examiner* — Shirley V Gembeh

(57) ABSTRACT

The present invention relates to a topical solution comprising a retinoid or its pharmaceutically acceptable salts thereof and a process of preparing it.

4 Claims, No Drawings

(56) References Cited

OTHER PUBLICATIONS

Anonymous, "Keratolytics", *Martindale: The Complete Drug Reference*(2010) [Accessed on Mar. 13, 2018] (Available from: https://www.medicinescomplete.com/mdmartindale/current/1590-a2-6-v.htm?q=KERATOLytics&t=search&ss=text&tot=8&p=1#_hit).
Anonymous, "Benzoates", *Martindale: The Complete Drug Reference* (2017) [Accessed on Mar. 13, 2018] (Available from: https://www.medicinescomplete.com/mc/martindale/current/ms-11730-m.htm?q=benzoic%20acid&t=search&ss=text&tot=262&p=1#_hit).
PCT Application No. PCT/IB2010/052254 filed May 20, 2010, published as WO 2010/134047 dated Nov. 25, 2010.
International Search Report and Written Opinion for International Application No. PCT/IB2010/052254 issued by PCT dated Sep. 13, 2011.
International Preliminary Report on Patentability for International Application No. PCT/IB2010/052254 issued by PCT dated Dec. 1, 2011.
International Search Report and Written Opinion for International Application No. PCT/IB2010/052255 issued by PCT dated Nov. 23, 2011.
International Preliminary Report on Patentability for International Application No. PCT/IB2010/052255 issued by PCT dated Dec. 15, 2011.
Restriction Requirement for U.S. Appl. No. 13/320,164, issued by USPTO dated Dec. 6, 2012.
Office Action for U.S. Appl. No. 13/320,164, issued by USPTO dated Apr. 10, 2013.
Final Office Action for U.S. Appl. No. 13/320,164, issued by USPTO dated Jul. 31, 2013.
Office Action for U.S. Appl. No. 13/320,164, issued by USPTO dated Feb. 6, 2015.
Final Office Action for U.S. Appl. No. 13/320,164, issued by USPTO dated Oct. 2, 2015.
Office Action for U.S. Appl. No. 13/320,164, issued by USPTO dated Nov. 28, 2016.
Restriction Requirement for U.S. Appl. No. 15/225,917, issued by USPTO dated Mar. 20, 2017.
Restriction Requirement for U.S. Appl. No. 15/444,491, issued by USPTO dated Mar. 23, 2017.
Co-pending U.S. Appl. No. 15/444,491, filed Feb. 28, 2017, not yet published.
Co-pending U.S. Appl. No. 15/225,917, filed Aug. 2, 2016, published as U.S. 2016/0338985 dated Nov. 24, 2016.
Office Action for U.S. Appl. No. 15/225,917, issued by USPTO dated Aug. 21, 2017.
Office Action for U.S. Appl. No. 15/444,491, issued by USPTO dated Sep. 26, 2017.
Final Office Action for U.S. Appl. No. 15/225,917, issued by USPTO dated Jan. 22, 2018.
Office Action dated Mar. 21, 2018 for EP Divisional Patent Application No. 15165623.8.

* cited by examiner

TOPICAL RETINOID SOLUTIONS

FIELD OF THE INVENTION

The present invention relates to a topical solution comprising a retinoid or its pharmaceutically acceptable salts thereof and a process for its preparation thereof.

BACKGROUND OF THE INVENTION

Acne is a disease of the skin in which the pilosebaceous structures of the skin become inflamed, leading to the formation of comedones, pustules and nodules. It is generally believed that acne arises when hyperkeratosis of the pilosebaceous structure wholly or partially blocks the opening of the structure, resulting in comedones filled with sebum, keratin, and *Propionibacterium acnes* ("*P. acnes*"). These lesions are commonly identified as acne. *P. acnes* naturally occurs in normal skin, but is especially and characteristically present in acne lesions. It is believed that metabolic byproducts and waste from *P. acnes* within the pilosebaceous structures cause or contribute to the inflammation of acne lesions.

Acne naturally varies in severity from mild to very severe. People with mild (superficial) acne develop only a few noninflamed blackheads or a moderate number of small, mildly irritated pimples, mostly on the face. Blackheads appear as tiny, dark dots at the center of a small swelling of normal-colored skin. Pimples are mildly uncomfortable and have a white center surrounded by a small area of reddened skin. People with severe (deep, or cystic) acne, on the other side, have numerous large, red, painful pus-filled lumps (nodules) that sometimes even join together under the skin into giant, oozing abscesses.

Depending on the degree of severity and pronounced appearance, one speaks of acne vulgaris, acne comedonica, acne papulo pustulosa, acne conglobata, etc. Further, the acne can be subdivided into two categories, inflammatory acne and non-inflammatory acne, based on both pathophysiological and therapeutic differences.

Conventional acne treatments have taken many forms. Oral drugs including antibiotics like tetracycline, minocycline, doxycycline, and erythromycin, and topical keratolytic agents, such as salicylic acid are sometimes used. Keratolytic agents are thought to encourage the opening up of blocked pilosebaceous structures, thereby reducing conditions that are favorable to inflammation. Benzoyl peroxide, an anti-microbial, remains a popular and effective treatment. Topical antibiotics, such as clindamycin, which are effective against *P. acnes*, have also been used with a view towards preventing the formation of metabolic byproducts from this organism.

A treatment option for acne is retinoids, which have been widely described in the past for treatment of a number of dermatological disorders, including acne and seborrhoea. Orally administered 13-cis retinoic acid (isotretinoin) revolutionized the treatment of severe forms of acne when it was introduced in 1982, and continues in the present to be the single therapy capable of curing severe acne. Oral isotretinoin is so effective against acne because it is the only treatment affecting all major etiological factors, including, in particular, a substantial reduction of sebum production by inhibition of the lipogenesis, as well as a reduction of the size of sebaceous glands of the patient. Thus, oral isotretinoin was established in the last decade as the gold standard of acne therapy, capable of long-term remission in about 80% of patients with severe acne.

Retinoids are known to possibly cause several serious side-effects, in particular when administered systemically, like birth defects; mental health problems including suicide danger; uncontrolled increases of brain pressure which can, e.g., lead to permanent loss of sight; damage of liver, pancreas, bowel and esophagus; possible bone and muscle problems; development of high levels of cholesterol and other fats in the blood; and others. However, retinoid formulations when administered topically would certainly represent an improvement with regard to the risk of possible side effects because of the substantially shorter way of the drug from the point of administration to the point of action associated with topical administration that results in a lower systemic exposure; hence topical therapy may be preferable over oral retinoid therapy.

A number of topical retinoid formulations are commercially available in the form of creams, gels, lotions, ointments and solutions. However the available topical dosage forms have been reported to produce skin irritation (dermatitis) which may be characterized by erythema, scaling, peeling, drying, pruritus, and sensations similar to sunburn. This problem is described in U.S. Pat. No. 4,888,342. Other side effects have also been reported with topical retinoids like itching, stinging or burning. Rarely edema, and blistering or crusting of skin may occur. Temporary hypopigmentation or hyperpigmentation has been reported in a few individuals treated with tretinoin. Temporary depigmentation in non-caucasians is possible.

Retinoids are insoluble or at most very slightly soluble in water, but readily soluble in, e.g., ethanol. Therefore retinoid containing preparations have been most effectively applied using an alcohol containing carrier system, which causes an uncomfortable burning sensation by itself. This sensation is amplified when applied to skin which was previously or is simultaneously treated with retinoic acid. Most of the topical retinoids formulations available in the market, like ISOTREX gel, ISOTREXIN gel, DIFFERIN (adapalene) solution and RETIN-A (tretinoin) solution, SOLAGE (mequinol and tretinoin) solution contain alcohol which have been reported to have an irritant effect on the skin.

WO 90/14833 discloses an aqueous composition for topical application to the skin, comprising a retinoid with ethanol and surfactant. Said composition comprises 0.1 to 20 wt % of a solubilising agent (ethanol) and a surfactant.

Most of the prior art discloses the use of an additional agent to reduce the skin irritation caused by formulations containing anti acne agent. These additional agents add an unnecessary load to the formulation.

U.S. Pat. No. 5,252,604 discloses the use of tocopherol such as alpha tocopherol in the topical composition of retinoic acid to overcome the problem of retinoic acid induced dermatitis resulting from topical retinoic acid application as tocopherol has free radical scavenging antioxidant properties.

U.S. Pat. No. 4,593,046 discloses a method of reducing skin irritation from benzoyl peroxide by the use of aloe vera which helps to reduce specific undesirable reactions which would otherwise result from the use of benzoyl peroxide to treat skin lesions.

U.S. Pat. No. 6,277,881 discloses the use of turmeric extract as an anti-irritant/anti-sting agent in the compositions containing hydroxy acids and/or retinoids.

U.S. Pat. No. 5,643,584 discloses a retinoid aqueous gel composition having effective amount of micronized retinoid particles, a surfactant to enhance penetration of retinoid into the skin, a preservative and a gelling agent. The invention also included polyvinylpyrrolidone to inhibit crystal growth of the micronized retinoids.

Cream formulations were found to be generally more acceptable to patients, but they were not without disadvantages, such as a reduced clinical effectiveness as compared with alcoholic compositions containing the same amount of retinoic acid. Aqueous retinoic acid preparations containing no alcohol and no fats have not shown to be clinically very effective, due to the fact that the active ingredient is not dissolved and, thus, not available for exerting the desired effect.

Thus, there exists a need for a composition comprising a retinoid, which is chemically and physically stable, that is alcohol-free and surfactant-free, yet is able to provide solubilized retinoid immediately and is clinically effective as a prior art compositions, with minimal or no skin irritation.

SUMMARY OF THE INVENTION

In one general aspect the present invention provides for a topical composition in the form of solution. The solution includes: (i) a therapeutically effective amount of a retinoid or its pharmaceutically acceptable salts thereof; (ii) a pharmaceutically acceptable vehicle; and (iii) one or more pharmaceutically acceptable excipients, wherein the composition is alcohol-free. The topical composition is stable during storage at 40° C. and 75% RH and 25° C. and 60% RH.

Embodiments of the invention may include one or more of the following features. For example, the retinoid is present in a concentration from about 0.001% to about 1.5% by weight per volume of the total composition. The retinoid may be tazarotene, retinoic acid, tretinoin, isotretinoin, adapalene, bexarotene, alitretinoin, vitamin A, retinol, retinal, retinyl palmitate, retinyl acetate, ethyl 5-(2-(4,4-dimethylthiochroman-6-yl)ethynyl)thiophene-2-carboxylate, 6-(2-4,4-dimethylthiochroman-6-yl)-ethynyl)-3-pyridylmethanol, 2-(2-(4,4-dimethylthiochroman-6-yl)-ethynyl)-5-pyridinecarboxaldehyde. For example, the retinoid is isotretinoin.

The vehicle may be lipophilic and may include one or more of fatty acid esters, fatty acids, fatty alcohols or vegetable oils. The pharmaceutically acceptable excipient may include one or more of colorants, fragrances, odor modifiers, viscosity modifiers, propellants, chelating agents, solubilizing excipients, penetration enhancers, preservatives, antioxidants, stabilizers, cleansing agent, moisturizers, humectants, emollients, astringents, keratolytics, moisturizers, sun filters and mixtures thereof including other optional components, which are soluble or miscible with the pharmaceutically acceptable carrier.

The topical composition may also include an additional active ingredient. The additional active ingredient is selected from antibiotics, bactericidal drugs, bacteriostatic drugs, anti-infective agents and anti-inflammatory agents.

In another general aspect, there is provided a method for treating acne or other skin related disorders. The method includes applying a topical solution, which includes: (i) a therapeutically effective amount of a retinoid or its pharmaceutically acceptable salts thereof; (ii) a pharmaceutically acceptable vehicle; and (iii) one or more pharmaceutically acceptable excipients, wherein the composition is alcohol-free.

In yet another general aspect, there is provided a topical composition in the form of solution, wherein the topical composition includes a retinoid or its pharmaceutically acceptable salt thereof, a pharmaceutically acceptable vehicle, and one or more pharmaceutically acceptable excipients, substantially as described and illustrated herein.

DETAILED DESCRIPTION OF THE INVENTION

The present invention relates to an alcohol free topical composition in the form of solution including:
 (i) a therapeutically effective amount of a retinoid or a pharmaceutically acceptable salts thereof;
 (ii) a pharmaceutically acceptable vehicle; and
 (iii) one or more pharmaceutically acceptable excipients, wherein the composition is alcohol-free.

As used herein the abbreviation "RH" stands for "Relative Humidity". As used herein, the phrase a "therapeutically effective amount" of an active agent refers to an amount of the pharmaceutically or pharmacologically active agent sufficient enough to have a positive effect on the area of application. Accordingly, these amounts are sufficient to modify the skin disorder, condition, or appearance to be treated but low enough to avoid serious side effects, within the scope of sound medical or dermatological advice. A therapeutically effective amount of the pharmaceutically pharmacologically active agent will cause a substantial relief of symptoms when applied repeatedly over time. Effective amounts of the pharmaceutically pharmacologically active agent will vary with the particular condition or conditions being treated, the severity of the condition, the duration of the treatment, the specific components of the composition being used, and other factors.

Retinoids available for use in the present inventive subject matter include all natural and synthetic retinoids. Non-limiting examples of retinoids useful in the present compositions include tazarotene, retinoic acid, tretinoin, isotretinoin, adapalene, bexarotene, alitretinoin, vitamin A, retinol, retinal, retinyl palmitate, retinyl acetate, ethyl 5-(2-(4,4-dimethylthiochroman-6-yl)ethynyl)thiophene-2-carboxylate, 6-(2-4,4-dimethylthiochroman-6-yl)-ethynyl)-3-pyridylmethanol, 2-(2-(4,4-dimethylthiochroman-6-yl)-ethynyl)-5-pyridinecarboxaldehyde, salts thereof, derivatives thereof, and mixtures thereof. Tazarotene, adapalene, tretinoin, and isotretinoin, as well as salts or derivatives thereof, are especially preferred in this regard. In the most preferred embodiment, the retinoid is isotretinoin or a salt or derivative thereof. Pharmaceutically acceptable salts, esters, or derivatives of retinoids refer to those that possess the desired pharmacological activity and are neither biologically nor otherwise undesirable.

The retinoid component of the present composition is present at a concentration from about 0.001% to about 1.5% by weight per volume of the total composition, and more preferably, in a concentration from about 0.01% to about 0.5% by weight per volume of the total composition.

In formulating the composition, any conventional non-toxic, non-irritant and dermatologically acceptable base or vehicle in which the retinoids are soluble and stable are acceptable.

The vehicle used in the composition of the present invention includes a lipophilic vehicle selected from the group comprising fatty acid esters, fatty acids, fatty alcohols or vegetable oils.

Fatty acid esters include polyol esters of medium chain fatty acids. Polyol esters of medium chain fatty acids are selected from esters and mixed esters of glycerol, propylene glycol, polyglycerol and polyethylene glycol with medium chain fatty acids. Particularly the polyol ester of medium chain fatty acid is medium chain triglyceride or propylene glycol mono or diesters.

Medium chain triglycerides are medium chain ($C_6$ to $C_{12}$) fatty acid esters of glycerol. Examples of medium chain fatty acids include caproic acid, caprylic acid, capric acid and lauric acid. Commercially available examples of a medium chain triglycerides include Neobee® 0 and Neobee® M5, Miglyol® 810, 812, 818 and 829; Captex® 350, 355 and 810D, Labrafac™ lipophile WL 1349, Crodamol™ GTCC. Medium chain triglycerides are very stable to oxidation.

Propylene glycol mono or diesters include propylene glycol monolaurate, propylene glycol monomyristate, propylene glycol dicaprylate/dicaprate. Commercially available examples of propylene glycol dicaprylate or dicaprate include Miglyol® 840, Captex® 200P, Labrafac™ PG, Estol® 1526, Mazol® PG-810, Neobee® M-20.

Further examples of fatty acid esters may include Capryol™ PGMC, Capryol™ 90, Lauroglyocol™ FCC, Lauroglycol™ 90, Transcutol® HP.

Specific examples of fatty acids include $C_6$-$C_{20}$ saturated or mono or di-unsaturated acid for example oleic acid, linoleic acid, caprylic acid or caproic acid.

Specific examples of fatty alcohols used in the compositions of the present invention include $C_6$-$C_{20}$ saturated or mono or di-unsaturated alcohol for example oleyl alcohol, capryl alcohol or capric alcohol.

Specific examples of vegetable oil used in the compositions of the present invention include kernel oil, almond oil, groundnut oil, olive oil, soybean oil, sunflower oil, palm oil, sesame oil, canola oil or corn oil or mixtures thereof. Particularly, the vegetable oil used in the compositions of the present invention is olive oil or soybean oil.

Particularly the vehicle used in the compositions of the present invention is selected from fatty acid esters or a vegetable oil or mixtures thereof.

Further, the vehicles used in the composition of the present invention are characterized by their acid value, hydroxyl value, iodine value, peroxide value and saponification value.

The "acid value" may be defined as the number of mg of potassium hydroxide (KOH) required to neutralize 1 g of a sample. It has been observed that the lower the acid value, the higher the stability of the composition. The vehicle used in the composition should have an acid value less than 1, particularly less than 0.5, and more particularly less than 0.2.

"Hydroxyl Value" is a measure of hydroxyl (univalent OH) groups in an organic material. It has been observed that the lower the hydroxyl value, the higher the stability of the composition. The vehicle used in the composition should have a hydroxyl value of less than 100, particularly less than 50, and more particularly less than 10.

"Iodine Value" is a measure of the unsaturation of fats and oils and is expressed in terms of the number of centigrams of iodine absorbed per gram of sample (% iodine absorbed). It has been observed that the lower the iodine value, the higher the stability of the composition. The vehicle used in the composition should have an iodine value of less than 10, preferably less than 5, and more preferably less than 1.

"Peroxide Value" is a measure of the extent of fat or oil oxidation of a substance by measuring the amount of peroxides present. Peroxides are intermediate compounds formed during the oxidation of lipids which may react further to form the compounds that can cause rancidity. It has been observed that the lower the peroxide value, the higher the stability of the composition. The vehicle used in the composition should have a peroxide value of less than 10, particularly less than 6, and more particularly less than 1.

"Saponification Value" is the amount of alkali necessary to saponify a definite quantity of a substance. It is commonly expressed as the number of milligrams of potassium hydroxide (KOH), or Sodium Hydroxide (NaOH), required to saponify 1 gram of the substance. It has been observed that the higher the saponification value, the higher the stability of the composition. The vehicle used in the composition should have a saponification value of higher than 200, particularly higher than 250, and more particularly higher than 300.

The composition of the present invention may further include one or more pharmaceutically acceptable excipients such as like antioxidants, preservatives, colorants, fragrances, odor modifiers, viscosity modifiers, propellants, chelating agents, solubilizing excipients, penetration enhancers, stabilizers, any of which are well known in the art. In addition, the composition may contain emollients, humectants, astringents, keratolytics, moisturizers, cleansing agent, sun filters and mixtures thereof. The composition may also include any pharmaceutically acceptable excipients that are soluble or miscible with lipophilic vehicle of the present invention to enhance the physical and/or chemical and/or microbiological stability of the retinoid composition.

Suitable antioxidants are frequently used in formulations for a number of reasons. A primary function of any antioxidant is to prevent oxidative degradation of the formulation containing it, by scavenging oxygen radicals in the environment. An effective antioxidant may also act to prevent or reduce microbial growth, and therefore prevent spoilage of the vehicle. Both these activities can contribute to the overall stability of the formulation.

Suitable antioxidants used in the present invention include butylated hydroxyl anisoles (BHA), butylated hydroxyl toluene (BHT), ethoxyquin, ascorbyl palmitate, citric acid, thiols, sulphoximines, metal chelators, fatty acids, vitamins, phenols, stilbenes, uric acid, mannose, isoflavones, selenium and propyl gallate.

The composition of the invention may also include preservatives. Preservatives are used in the topical composition to prevent the growth of microorganisms (e.g., bacteria, fungi, yeasts) therein. Preferably, the preservative must be effective at relatively low concentrations against a broad spectrum of microorganisms. In addition, the preservative must be non-toxic at the required concentration, compatible with other ingredients in the topical composition, stable to the expected preparation and storage conditions, and approved by global regulatory agencies. The composition of the present invention may include more than one preservative. A blend of preservatives can facilitate a broader spectrum of antimicrobial activity if the individual preservatives of the blend are effective against different microorganisms.

Suitable preservatives used in the composition include quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other anti-microbial agents such as chlorhexidine, chlorocresol, benzoic acid and polymyxin.

Emollients are skin softeners. Examples of emollients include hydrocarbon oils, waxes, or silicones. Astringents are drying agents that precipitate protein and shrink and contract the skin. Examples of astringents include aluminum sulfate and calcium acetate. Keratolytics are agents that soften, loosen, and facilitate exfoliation of the squamous cells of the epidermis. Examples of keratolytics include sulfur, resorcinol and salicylic acid. Humectants are used to moisturize the skin and may include glycerine, propylene glycol and glyceryl triacetate. Sun filters may include titanium dioxide, zinc oxide and mixtures thereof.

The composition of the present invention may also include an additional active ingredient that including other retinoids or its derivatives, antibiotics, bactericidal drugs, bacteriostatic drugs, anti-infective agents and anti-inflammatory agents.

Examples of antibiotic agents for use herein include macrolides such as azithromycin, clarithromycin, lincomycin, clindamycin, erythromycin, pharmaceutically acceptable salts and esters thereof and the like and mixtures thereof.

The macrolides are similar in structure and activity. All the macrolides are easily absorbed, are primarily bacteriostatic and bind to the 50S subunit of the ribosome, thus inhibiting bacterial protein synthesis. These drugs are active against aerobic and anaerobic gram-positive cocci, with the exception of enterococci, and against gram-negative anaerobes and useful in the present compositions.

Examples of bactericidal drugs (i.e., kill bacteria) include penicillins, cephalosporins, vancomycin, aminoglycosides, quinolones, and polymyxins.

Examples of bacteriostatic drugs (i.e., slow bacterial growth) include, but are not limited to, erythromycin, tetracyclines, chloramphenicol, lincomycin, clarithromycin, azithromycin, and sulfonamides. However, it is well know that some bactericidal drugs may be bacteriostatic against certain microorganisms and vice versa.

Suitable anti-infective agents may include the topically applicable antibacterial, anti-yeast and anti-fungal agents.

In addition to acne treatment, the present composition may be used for the treatment of a variety of skin conditions, including impetigo, rosacea, psoriasis, atopic dermatitis, secondary skin infections, responsive dermatoses, and combinations thereof. Other specific skin disorders treatable by the present topical composition include seborrhea and skin lesions.

The composition of the present invention may be applied to the skin by either directly layering on or spreading or spraying on epidermal tissue, especially outer skin. The composition of the present invention can be filled into suitable packaging components to deliver a uniform, reproducible and small amount of the composition through topical route.

The present invention is illustrated below by reference to the following examples. However, one skilled in the art will appreciate that the specific methods and results discussed are merely illustrative of the invention, and not to be construed as limiting the invention.

EXAMPLES

Examples 1 and 2

| S. No. | Ingredients | Example 1 Composition (w/v) | | Example 2 Composition (w/v) | |
|---|---|---|---|---|---|
| | | 0.05% | 0.1% | 0.05% | 0.1% |
| 1 | Isotretinoin | 0.05 | 0.10 | 0.05 | 0.10 |
| 2 | Butylated hydroxyl anisole | 0.05 | 0.05 | 0.05 | 0.05 |
| 3 | Benzoic acid | 0.025 | 0.025 | 0.025 | 0.025 |
| 4 | Propylene glycol dicaprylate/ dicaprate (vehicle) | q.s. | q.s. | — | — |
| 5 | Caprylic/capric triglyceride (vehicle) | — | — | q.s. | q.s. |

Procedure:
1. Butylated hydroxyl anisole was dissolved in a lipophilic vehicle under continuous stirring.
2. Isotretinoin was dissolved in the solution of step 1 at 40°-45° C. with continuous stirring to form clear solution.
3. The solution of step 2 was cooled down to room-temperature and benzoic acid was dissolved under stirring to form homogenous solution.

Examples 3 and 4

| S. No. | Ingredients | Example 3 Composition (w/v) | | Example 4 Composition (w/v) | |
|---|---|---|---|---|---|
| | | 0.05% | 0.1% | 0.05% | 0.1% |
| 1 | Isotretinoin | 0.05 | 0.10 | 0.05 | 0.10 |
| 2 | Butylated hydroxyl anisole | 0.05 | 0.05 | 0.05 | 0.05 |
| 4 | Propylene glycol dicaprylate/ dicaprate (vehicle) | q.s. | q.s. | — | — |
| 5 | Caprylic/capric triglyceride (vehicle) | — | — | q.s. | q.s. |

Procedure:
1. Butylated hydroxyl anisole was dissolved in a lipophilic vehicle under continuous stirring.
2. Isotretinoin was dissolved in the solution of step 1 at 40°-45° C. with continuous stirring to form clear solution.
3. The solution of step 2 was cooled down to room-temperature.

Example 5

Table 1 shows the stability data of 0.1% w/v composition prepared according to Example 1.

TABLE 1

| | | 40° C./75% RH | | | 25° C./ 60% RH |
|---|---|---|---|---|---|
| | Initial | 1 month | 2 month | 3 month | 3 month |
| Assay(% Claim) | 98.0 | 101.0 | 100.0 | 99.0 | 98.0 |
| BHA (% Claim) | 102.0 | 102.0 | 104.0 | 102.0 | 102.0 |
| BA (% Claim) | 98.4 | 99.2 | 98.4 | 98.0 | 98.0 |
| Total RS | 1.314 | 1.346 | 1.847 | 1.950 | 1.631 |

Example 6

Table 2 shows the stability data of 0.05% w/v composition prepared according to Example 1.

TABLE 2

|  | Initial | 40° C./75% RH | | | 25° C./ 60% RH |
|---|---|---|---|---|---|
|  |  | 1 month | 2 month | 3 month | 3 month |
| Assay(% Claim) | 98.0 | 100.0 | 100.0 | 100.0 | 98.0 |
| BHA (% Claim) | 102.0 | 100.0 | 102.0 | 102.0 | 102.0 |
| BA (% Claim) | 89.2 | 89.2 | 88.4 | 88.4 | 89.6 |
| Total RS | 1.628 | 1.861 | 2.264 | 2.436 | 1.968 |

Example 7

Table 3 shows the stability data of 0.1% w/v composition prepared according to Example 3.

TABLE 3

|  | Initial | 40° C./75% RH | | | | 25° C./ 60% RH |
|---|---|---|---|---|---|---|
|  |  | 1 month | 2 month | 3 month | 6 month | 6 month |
| Assay(% Claim) | 102.9 | 97.0 | 97.0 | 97.0 | 96.0 | 99.0 |
| BHA (% Claim) | 104.0 | 102.0 | 102.0 | 102.0 | 106.0 | 104.0 |
| Total RS | 1.015 | 1.249 | 1.244 | 1.731 | 1.940 | 1.638 |

Example 8

Table 4 shows the stability data of 0.05% w/v composition prepared according to Example 3.

TABLE 4

|  | Initial | 40° C./75% RH | | | | 25° C./ 60% RH |
|---|---|---|---|---|---|---|
|  |  | 1 month | 2 month | 3 month | 6 month | 6 month |
| Assay(% Claim) | 101.4 | 98.0 | 98.0 | 98.0 | 96.0 | 98.0 |
| BHA (% Claim) | 108.0 | 108.0 | 108.0 | 106.0 | 106.0 | 106.0 |
| Total RS | 1.229 | 1.573 | 1.335 | 1.850 | 2.012 | 1.688 |

Example 9

Table 5 shows the stability data of 0.05% w/v composition prepared according to Example 4.

TABLE 5

|  | Initial | 40° C./75% RH | | | | 25° C./ 60% RH |
|---|---|---|---|---|---|---|
|  |  | 1 month | 2 month | 3 month | 6 month | 6 month |
| Assay(% Claim) | 101.3 | 99.3 | 96.9 | 99.6 | 94.8 | 97.2 |
| BHA (% Claim) | 101.4 | 101.8 | 99.2 | 99.4 | 97.6 | 99.8 |
| Total RS | 0.313 | 0.837 | 1.201 | 1.311 | 1.693 | 1.085 |

Example 10

The isotretinoin topical solution 0.1% w/v of the present invention prepared according to Example 3 was subjected to single dose dermal irritation study in male New Zealand white rabbits. The study was compared with isotretinoin gel at a concentration of 0.05% w/w.

A total 6 male New Zealand White Rabbits were randomly distributed into two groups consisting of 3 animals/group. The different formulations of the test item and placebo were applied to either the right dorso-lateral trunk region or left dorso-lateral trunk region of the each animal (based on site randomization). The three patches of test item, isotretinoin gel 0.05% w/w, isotretinoin topical solution 0.1% w/v were applied simultaneously to two animals and additionally the placebo for isotretinoin topical solution was also applied to one male. One patch of each isotretinoin gel 0.05% w/w, isotretinoin topical solution 0.1% w/v and placebo for isotretinoin topical solution were removed at 3 minutes and 1 hour post exposure period. No signs of irritation were noticed during 3 minutes and 1 hour exposure period to the first group of rabbits. The additional four rabbits were exposed with a single patch of either isotretinoin gel 0.05% w/w, isotretinoin topical solution 0.1% w/v or placebo for isotretinoin topical solution for period of 4 hours. The third patch of these test items and placebo applied to first two rabbits were also exposed for 4 hours. All the animals were examined for signs of erythema and edema and the responses were scored at 1 hour, 24 hours, 48 hours and 72 hours post exposure period (4 hours). Additionally two males which were exposed to single patch for 3 minutes and 1 hour exposure period were also examined for signs of erythema and edema at 5 minutes and 10 minutes post exposure respectively. No signs of erythema and edema were noticed after the 3 minute and 1 hour exposure periods for isotretinoin gel 0.05% w/w and isotretinoin topical solution 0.1% w/v. No signs of erythema and edema were noticed after a single dose dermal application (4 hour exposure) of isotretinoin topical solution 0.1% w/v and placebo for isotretinoin topical solution 0.1% w/v up to 14 days. A single dose dermal application (4 hour exposure) of isotretinoin gel 0.05% w/w caused well defined erythema at 1 hour, which developed to severe erythema at 24 hours and remained up to 72 hours post exposure. The signs of recovery were noticed beginning on day 5 onwards and with full recovery on day 14. In another rabbit single dose dermal application (4 hour exposure) of isotretinoin gel 0.05% w/w, very slight erythema formation at 1 hour was present which developed into well defined erythema at 24 hours and remained for up to 72 hours post exposure. Signs of recovery were noticed beginning on day 5 onwards and with full recovery on day 8. Edema (very slight) was noticed in two rabbits after single dose dermal application (4 hour exposure) of isotretinoin gel 0.05% w/w at 1 hour with complete recovery at 72 hours post application. No dermal irritation potential was seen in isotretinoin topical solution 0.1% w/v of present invention.

Example 11

The isotretinoin topical solutions of 0.05% w/v and 0.1% w/v of the present invention prepared according to Example 1 were subjected to a 28-day repeat dose dermal local tolerance study in male New Zealand white rabbits.

A total of 9 male New Zealand White Rabbits were used. The different formulations of the test item and/or placebo were applied topically to each animal on the test sites covering approximately 10% of the total body surface area, either on abraded skin or intact skin. A quantity of 500 μl of isotretinoin topical solution 0.05% w/v or isotretinoin topical solution 0.1% w/v or placebo for isotretinoin topical solution was applied for 28 consecutive days. The four patches of test item; isotretinoin topical solution 0.05% w/v or isotretinoin topical solution 0.1% w/v or placebo for isotretinoin topical solution were applied simultaneously to all the animals. All the animals were examined for signs of erythema and edema formation and responses were scored once daily at 1 to 2 hours post-4 hours exposure (Table 6). Erythema and edema formation were scored on a scale of 0 to 4 with score 0 indicating no erythema and no edema, while a score of 4 indicated severe erythema and severe edema.

TABLE 6

| Type of site | Dermal Application | Erythema Score | Edema Score |
| --- | --- | --- | --- |
| Abraded Skin | Placebo for Isotretinoin Topical Solution | 0.00 | 0 |
|  | Isotretinoin Topical Solution 0.05% w/v | 0.00 | 0 |
|  | Isotretinoin Topical Solution 0.1% w/v | 0.24 | 0 |
| Intact skin | Placebo for Isotretinoin Topical Solution | 0.00 | 0 |
|  | Isotretinoin Topical Solution 0.05% w/v | 0.04 | 0 |
|  | Isotretinoin Topical Solution 0.1% w/v | 0.23 | 0 |

All the animals were euthanized on day 29. Skin tissue samples (application sites) were collected from each animal and processed as per standard methods. No microscopic changes noticed in any of the tissue samples evaluated. No dermal irritation and/or corrosive potential was noticed for isotretinoin topical solution in male New Zealand White Rabbits upon repeated dermal application for 28 consecutive days.

While several particular forms of the invention have been illustrated and described, it will be apparent that various modifications and combinations of the invention detailed in the text can be made without departing from the spirit and scope of the invention.

We claim:
1. A stable topical composition in the form of an unencapsulated single phase solution for applying to the skin of a human having a skin infection to treat the skin infection, the topical composition consisting of:
   (i) a therapeutically effective amount of isotretinoin or its pharmaceutically acceptable salts thereof as the sole active ingredient, the isotretinoin being present at a concentration of 0.05% or 0.1% by weight per volume of the total composition;
   (ii) a pharmaceutically acceptable vehicle selected from the group consisting of one or more of fatty acid esters, or fatty acids, or vegetable oils in which the therapeutically effective amount of isotretinoin is soluble; and
   (iii) one or more pharmaceutically acceptable excipients, wherein the composition is free of ethyl alcohol and the topical composition exhibits no skin irritation.

2. The composition according to claim 1, wherein the pharmaceutically acceptable excipient comprises one or more of colorants, fragrances, odor modifiers, viscosity modifiers, propellants, chelating agents, solubilizing excipients, penetration enhancers, preservatives, antioxidants, stabilizers, cleansing agent, moisturizers, humectants, emollients, astringents, keratolytics, moisturizers, sun filters and mixtures thereof.

3. The composition according to claim 1, wherein the composition is stable during storage at 40° C. and 75% RH and 25° C. and 60% RH.

4. A non-irritant stable topical composition in the form of an unencapsulated single phase solution, the topical composition consisting of:

| Ingredient | (w/v) |
| --- | --- |
| Isotretinoin | 0.05% or 0.1% |
| Antioxidant | 0.001%-5.00% |
| Lipophilic vehicle | 75%-99.90% | wherein the vehicle comprises compounds selected from the group consisting of one or more of fatty acid esters, or fatty acids, or vegetable oils.

* * * * *